United States Patent
Bush et al.

(10) Patent No.: US 10,984,900 B1
(45) Date of Patent: Apr. 20, 2021

(54) SYSTEMS AND METHODS FOR REFILLING PRESCRIPTIONS BY TEXT MESSAGE

(71) Applicant: Express Scripts Strategic Development, Inc., St Louis, MO (US)

(72) Inventors: Gabe Bush, Tampa, FL (US); James C Green, St. Louis, MO (US); Christina J Thach, Webster Groves, MO (US); Krystal A Salamon, St. Louis, MO (US); Stephanie A Wilton, St Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 154 days.

(21) Appl. No.: 16/256,217

(22) Filed: Jan. 24, 2019

(51) Int. Cl.
*G16H 20/10* (2018.01)
*H04W 4/14* (2009.01)

(52) U.S. Cl.
CPC .............. *G16H 20/10* (2018.01); *H04W 4/14* (2013.01)

(58) Field of Classification Search
CPC ........ G16H 20/10; G16H 40/20; G16H 80/00; G16H 40/67; H04W 4/14; H04W 40/244; H04W 4/023
USPC .......................................................... 705/2
See application file for complete search history.

(56) References Cited

U.S. PATENT DOCUMENTS

| | | | | |
|---|---|---|---|---|
| 8,626,530 | B1 * | 1/2014 | Tran | G06Q 50/22 705/2 |
| 2002/0138302 | A1 | 9/2002 | Bodnick | |
| 2003/0018495 | A1 * | 1/2003 | Sussman | G06Q 50/22 705/2 |
| 2007/0168228 | A1 | 7/2007 | Lawless | |
| 2008/0238666 | A1 | 10/2008 | Loncar | |
| 2009/0287502 | A1 | 11/2009 | Roberts et al. | |
| 2011/0225004 | A1 * | 9/2011 | Loncar | G06F 19/3456 705/2 |
| 2013/0218595 | A1 | 8/2013 | Burkett | |

(Continued)

OTHER PUBLICATIONS

3Cinteractive Corp.: "In a Rapidly Changing Digital World, Mobile Expertise Matters: Our Expertise Is in Linking Mobile Marketing Services to Business Value"; <https://www.3cinteractive.com/company/expertise/> accessed Sep. 8, 2020.

(Continued)

*Primary Examiner* — Hiep V Nguyen
(74) *Attorney, Agent, or Firm* — Harness, Dickey & Pierce, PLC

(57) ABSTRACT

A messaging module is configured to, in response to a first indicator indicating that a patient has opted into receiving text messages, selectively send and receives text messages to and from a mobile phone number of the patient. A refill by text (RBT) module is configured to, when a second indicator indicates that the patient is not included in an RBT program, trigger the messaging module to send a predetermined text message to the mobile phone number in response to a determination that: a name of a prescription drug prescribed to the patient is included in a stored list of prescription drugs associated with the RBT program; the first indicator indicates that the patient has opted into receiving text messages; and a number of refills of the prescription drug already provided to the patient without a change in the therapy of the prescription drug is greater than a predetermined number.

26 Claims, 8 Drawing Sheets

(56) References Cited

U.S. PATENT DOCUMENTS

2017/0344724 A1 11/2017 Nockley
2017/0357774 A1 12/2017 Figg

OTHER PUBLICATIONS

Blink Health LLC "Your Medicine Delivered to Your Door"; Medication Home Delivery; <https://health.blinkhealth.com/medication-home-delivery/> Accessed Sep. 8, 2020.

KMart Pharmacy: "Auto Refills Never Forgets: Refilling Your Prescription is easy" <https://pharmacy.kmart.com/newrx-auto-refill> accessed Sep. 8, 2020.

O'Brien, Rob. "Pharmacy of the Future" CVSHealth Payor Solutions; Jun. 13, 2017.

Raley's; "Raley's Launches New Pharmacy Mobile App": <https://www.raleys.com/news/raleys-launches-new-pharmacy-mobile-app/> Accessed Sep. 8, 2020.

Schultz, Cory; "Refill your prescriptions with Walgreen's new text messaging program" MedicalApps Megpage Today; Oct. 18, 2011.

\* cited by examiner

Patient Profile — 504

- Patient
- Mobile Number
- Drug
- Therapy
- Authorized Refills
- Length of Unchanged Therapy
- Opt into Text Messaging (T/F)
- RBT (T/F)
- TFN Used for Messaging
- Email
- Mailing Address
- Billing information

FIG. 5

SYSTEMS AND METHODS FOR REFILLING PRESCRIPTIONS BY TEXT MESSAGE

FIELD

The present disclosure relates to systems and methods for refilling prescriptions and more particularly to systems and methods for refilling prescriptions via text messaging.

BACKGROUND

For some types of prescription drugs, a prescriber can authorize a prescription drug to be refilled one or more times without a patient obtaining a new prescription for the prescription drug. The patient may initiate a refill of the prescription drug, for example, via call or online with the pharmacy that initially fulfilled the prescription. The patient may retrieve the refill, once available, by traveling to the pharmacy.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a feature, a system for refilling prescription drugs by text messaging is described. A computer-readable medium stores patient profiles for patients, respectively. Each of the patient profiles includes at least: a name of a patient; a name of a prescription drug prescribed to the patient; a number of authorized refills of the prescription drug presently available to the patient; a number of refills of the prescription drug already provided to the patient without a change in a therapy of the prescription drug; a mobile phone number of the patient; a first indicator indicative of whether the patient has opted into receiving text messages; and a second indicator indicative of whether the patient is included in a refill by text (RBT) program. A messaging module is configured to, in response to the first indicator indicating that the patient has opted into receiving text messages, selectively send text messages to the mobile phone number of the patient and to receive text messages from the mobile phone number of the patient. An RBT module is configured to, when the second indicator indicates that the patient is not included in the RBT program, trigger the messaging module to send a first predetermined text message to the mobile phone number of the patient in response to a determination that: the name of the prescription drug prescribed to the patient is included in a stored list of prescription drugs associated with the RBT program; the first indicator indicates that the patient has opted into receiving text messages; and the number of refills of the prescription drug already provided to the patient without a change in the therapy of the prescription drug is greater than a predetermined number. The first predetermined text message offers entry into the RBT program to the patient.

In further features, the RBT module is configured to trigger the messaging module to send the second predetermined text message to the mobile phone number of the patient in response to a determination that: the second indicator indicates that the patient is included in the RBT program; the number of authorized refills of the prescription drug presently available to the patient is greater than zero; and a period since a last refill of the prescription drug by the patient is greater than a predetermined period.

In further features, the messaging module sends text messages to the mobile phone number of the patient from a toll free number (TFN) and receives text messages from the mobile phone number of the patient at the TFN.

In further features, the first predetermined text message includes the text: Reply YES to start text refills for med starting with <X>. The messaging module inserts a first letter of the name of the prescription drug in place of <X>.

In further features, the RBT module is configured to trigger the messaging module to send a third predetermined text message to the mobile phone number of the patient in response to receiving a text message including an unknown response to the first predetermined text message.

In further features, the RBT module is configured to change the second indicator to indicate that the patient is included in the RBT program in response to receiving a text message including an affirmative response to the first predetermined text message and verifying that the affirmative response is included in a stored list of affirmative responses.

In further features, the second predetermined text message includes the text: Reply YES to refill your med starting with <X>. The messaging module inserts a first letter of the name of the prescription drug in place of <X>.

In further features, the second predetermined text message includes the text: Reply YES to refill your med starting with <X> to be shipped to the address starting with <123>. The messaging module inserts a first letter of the name of the prescription drug in place of <X> and inserts a street address of the patient in place of <123>.

In further features, at least one pharmacy fulfillment device is configured to package the prescription drug for shipment to the patient in response to being triggered by the RBT module. The RBT module is configured to trigger the at least one pharmacy fulfillment device in response to receiving a text message from the mobile phone number of the patient including an affirmative response to the second predetermined text message.

In further features, the RBT module is configured to trigger the at least one pharmacy fulfillment device in response to receiving a text message from the mobile phone number of the patient including an affirmative response to the second predetermined text message and verifying that the affirmative response is included in a stored list of affirmative responses.

In further features, the at least one pharmacy fulfillment device is configured to dispense the prescription drug into a bottle in response to being triggered by the RBT module.

In further features, the at least one pharmacy fulfillment device is configured to apply a shipping label to the package in response to being triggered by the RBT module.

In further features, the messaging module is further configured to: receive a deactivated mobile numbers list from a cellular service provider; and in response to a determination that the mobile phone number of the patient is included in the deactivated mobile numbers list: set the first indicator to indicate that the patient has not opted into receiving text messages; and set the second indicator to indicate that the patient is not included in the RBT program.

In a feature, a method includes: selectively accessing a computer-readable medium storing patient profiles for patients, respectively, each of the patient profiles including at least: a name of a patient; a name of a prescription drug prescribed to the patient; a number of authorized refills of the prescription drug presently available to the patient; a number of refills of the prescription drug already provided to the patient without a change in a therapy of the prescription drug; a mobile phone number of the patient; a first indicator indicative of whether the patient has opted into receiving text messages; and a second indicator indicative of whether the patient is included in a refill by text (RBT) program; in response to the first indicator indicating that the patient has opted into receiving text messages, selectively sending text messages to the mobile phone number of the patient and receiving text messages from the mobile phone number of the patient; when the second indicator indicates that the patient is not included in the RBT program, sending a first predetermined text message to the mobile phone number of the patient in response to a determination that: the name of the prescription drug prescribed to the patient is included in a stored list of prescription drugs associated with the RBT program; the first indicator indicates that the patient has opted into receiving text messages; and the number of refills of the prescription drug already provided to the patient without a change in the therapy of the prescription drug is greater than a predetermined number, where the first predetermined text message offers entry into the RBT program to the patient; changing the second indicator to indicate that the patient is included in the RBT program in response to receiving a text message from the mobile phone number of the patient including an affirmative response to the first predetermined text message; and when the second indicator indicates that the patient is included in the RBT program and the number of authorized refills of the prescription drug presently available to the patient is greater than zero, sending a second predetermined text message to the mobile phone number of the patient, where the second predetermined text message requests a response indicative of whether the patient would like to initiate a refill of the prescription drug.

In further features, sending the second predetermined text message includes sending the second predetermined text message to the mobile phone number of the patient in response to a determination that: the second indicator indicates that the patient is included in the RBT program; the number of authorized refills of the prescription drug presently available to the patient is greater than zero; and a period since a last refill of the prescription drug by the patient is greater than a predetermined period.

In further features, the method further includes sending text messages to the mobile phone number of the patient from a toll free number (TFN) and receiving text messages from the mobile phone number of the patient at the TFN.

In further features, the first predetermined text message includes the text: Reply YES to start text refills for med starting with <X>. The method further includes inserting a first letter of the name of the prescription drug in place of <X>.

In further features, the method further includes sending a third predetermined text message to the mobile phone number of the patient in response to receiving a text message including an unknown response to the first predetermined text message.

In further features, the method further includes changing the second indicator to indicate that the patient is included in the RBT program in response to receiving a text message including an affirmative response to the first predetermined text message and verifying that the affirmative response is included in a stored list of affirmative responses.

In further features, the second predetermined text message includes the text: Reply YES to refill your med starting with <X>. The method further includes inserting a first letter of the name of the prescription drug in place of <X>.

In further features, the second predetermined text message includes the text: Reply YES to refill your med starting with <X> to be shipped to the address starting with <123>. The method further includes inserting a first letter of the name of the prescription drug in place of <X> and inserts a street address of the patient in place of <123>.

In further features, the method further include, by at least one pharmacy fulfillment device, packaging the prescription drug for shipment to the patient in response to receiving a text message from the mobile phone number of the patient including an affirmative response to the second predetermined text message.

In further features the method further includes, by at least one pharmacy fulfillment device, packaging the prescription drug for shipment to the patient in response to receiving a text message from the mobile phone number of the patient including an affirmative response to the second predetermined text message and verifying that the affirmative response is included in a stored list of affirmative responses.

In further features the method further includes, by the at least one pharmacy fulfillment device, dispensing the prescription drug into a bottle in response to receiving the text message from the mobile phone number of the patient including the affirmative response to the second predetermined text message and verifying that the affirmative response is included in the stored list of affirmative responses.

In further features the method further includes, by the at least one pharmacy fulfillment device, applying a shipping label to the package in response to receiving the text message from the mobile phone number of the patient including an affirmative response to the second predetermined text message and verifying that the affirmative response is included in the stored list of affirmative responses.

In further features, the method further includes: receiving a deactivated mobile numbers list from a cellular service provider; and in response to a determination that the mobile phone number of the patient is included in the deactivated mobile numbers list: setting the first indicator to indicate that the patient has not opted into receiving text messages; and setting the second indicator to indicate that the patient is not included in the RBT program.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

FIG. 5 is an example diagram of a patient profile that is stored in a computer-readable medium.

In the drawings, reference numbers may be reused to identify similar and/or identical elements.

DETAILED DESCRIPTION

Figure 1:
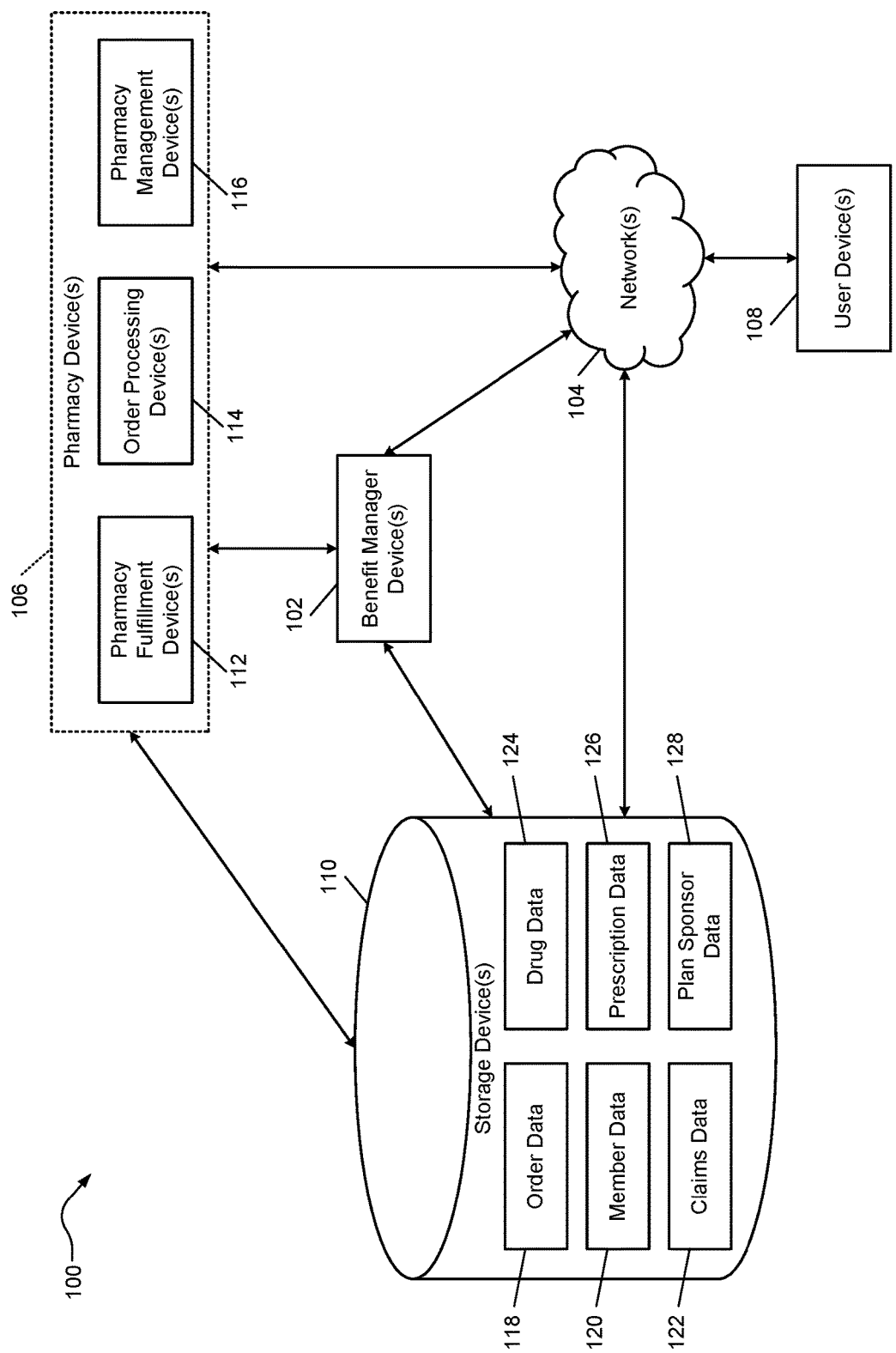
FIG. 1 is a functional block diagram of an example system including a high-volume pharmacy.

Drug prescribers can, under some circumstances, authorize one or more refills of a prescription drug for a patient. When a predetermined portion of the prescription drug should be remaining or less, the patient can refill the prescription via the pharmacy that initially filled the prescription. For example, the patient can initiate a refill of the prescription by physically travelling to the pharmacy, calling the pharmacy, or via a website of the pharmacy.

Some prescription drug therapies, such as some therapies involving specialty drugs, may remain unchanged for periods of time. Some patients, such as patients with therapies that treated consistently using the same medication or therapy regimen, would prefer the ability to initiate refilling of a prescription via text messaging. Text messaging may be a preferred mechanism for refilling prescriptions, for example, due to a patient's active and busy lifestyle, and the ability to conduct seamless, contained two-way interaction with the pharmacy.

According to the present application, when a patient is in a refill by text messaging (RBT) program of a pharmacy, the pharmacy (via one or more processors or other computing devices) sends a text message to a mobile phone number of the patient when the patient is eligible to refill their prescription. The text message asks whether the patient would like to refill their prescription. If the patient responds by text message back to the pharmacy with a predetermined affirmative response, such as yes, yes thank you, or yes please, the pharmacy initiates filling of the prescription for the patient. This may ensure that the medication is fulfilled and delivered prior to the patient's supply running out. The pharmacy may also package the refill for shipment and ship the packaged refill to a delivery address of the patient.

The ability to initiate refilling of the prescription via text message may provide an easier and more efficient way of initiating a refill than initiating refills in other ways. Because of the experience, patients may be more adherent to their medication and therapy regimen, and patients may be less likely to run out of a medication than if patients are required to initiate a refill.

The pharmacy may send a text message regarding the RBT program to the mobile phone number of the patient when predetermined conditions for entry into the RBT program of the pharmacy are satisfied. The text message may ask whether the patient would like to enter into the RBT program of the pharmacy. The predetermined conditions may include, for example, at least a predetermined number of refills of the prescription have already been performed without the therapy changing, the prescribed drug be on a predetermined drug list, and that the patient has already opted into receiving text messages from the pharmacy. If the patient responds by text message back to the pharmacy with a predetermined affirmative response, such as yes, yes thank you, or yes please, the pharmacy may add the patient to the RBT program. Once added to the RBT program, the patient can initiate refills by text message with the pharmacy, as discussed above.

Alternatively, patients that have enrolled in text messaging interaction with the pharmacy may be auto-enrolled into the RBT program. Instead of prompting an RBT program enrollment response from the patient, a refill text alert may be deployed to patients enrolled in text messaging programs and leveraging interactions to complete alternative tasks associated with their prescriptions that are on file.

Patients may deactivate their mobile phone numbers from time to time, such as when switching cellular service carriers, and under other circumstances. Each cellular service carrier periodically (e.g., daily) publishes a deactivated phone numbers list that includes the mobile phone numbers that it previously serviced but that have been deactivated since its last publication of its deactivated phone numbers list. When a patient that is in the RBT program has a mobile phone number that is on a deactivated phone number list, the pharmacy removes the patient from the RBT program. The pharmacy thereby avoids the possibility of sending text messages to people other than the patient.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may include a local area network or a global communication network, such as the Internet. In some implementations, the network 104 may include a network dedicated to prescription orders: a prescribing network such as the electronic prescribing network operated by Surescripts of Arlington, Va.

Moreover, although the network 104 is shown as a single network, the network 104 may include multiple networks. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as the order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
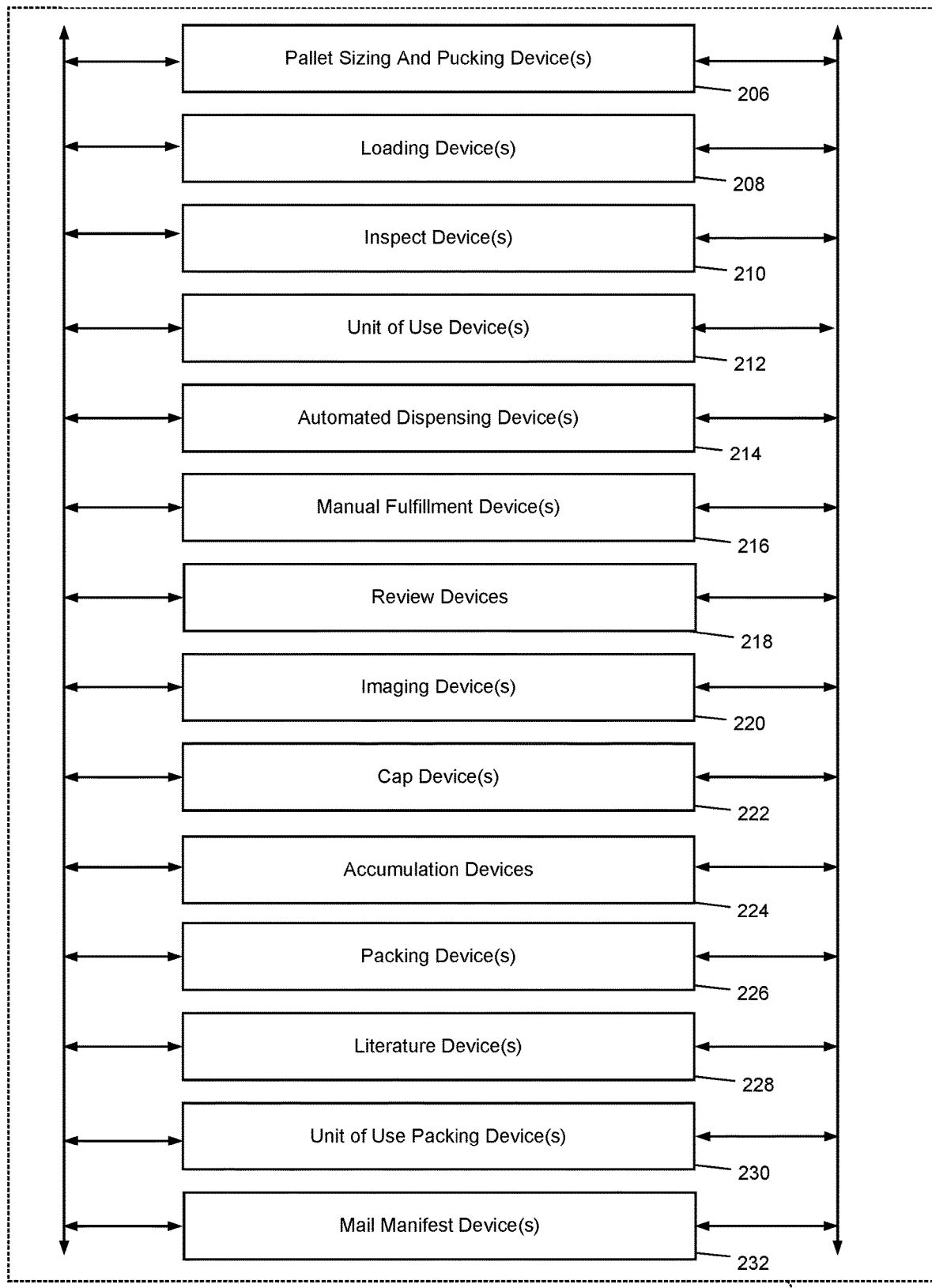
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as the order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing device(s) 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
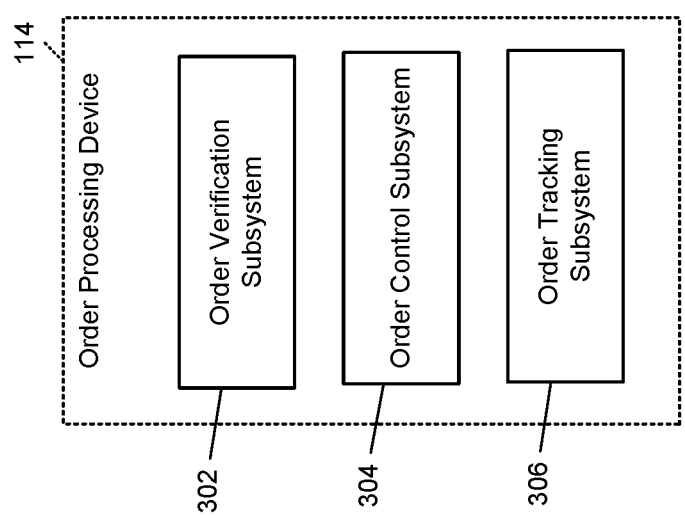
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Refill by Text System

Figure 4:
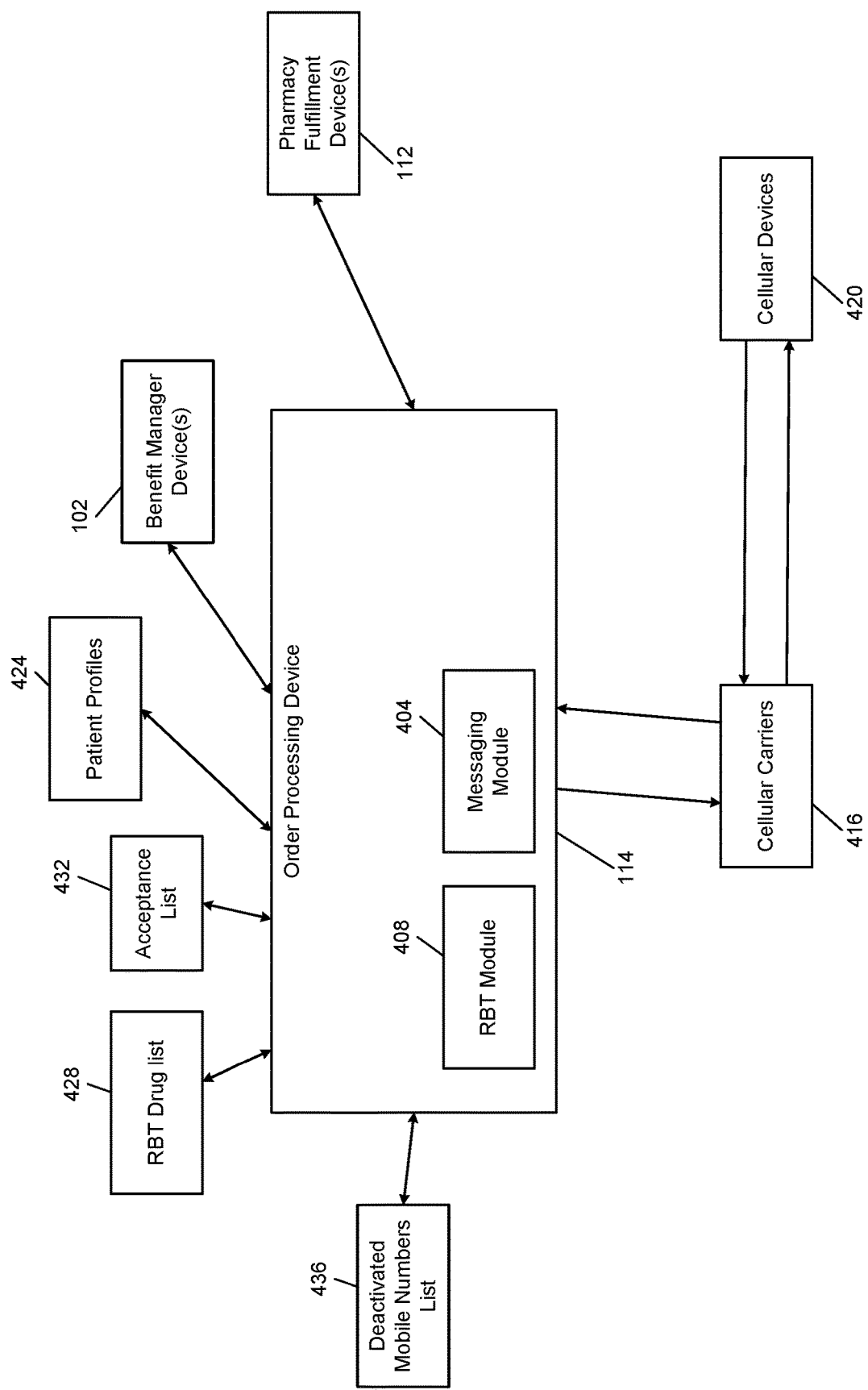
FIG. 4 is a functional block diagram of an example implementation of a refill by text (RBT) system.

FIG. 4 is a functional block diagram of an example implementation of a refill by text (RBT) system. The order processing device 114 may include a messaging module 404 that sends and receives text messages to and from patient mobile devices (e.g., cellular phones). An RBT module 408 controls enrollment of patients in an RBT program of the pharmacy and communicates, by text message, with patients that are enrolled in the RBT program. The RBT module 408 also initiates completion and shipment of authorized refills to patients in response to predetermined text message exchanges with patients enrolled in the RBT program.

The messaging module 404 sends and receives text messages to and from mobile devices of patients via one or more toll free numbers (TFNs) operated by the pharmacy. To send a text message to a mobile device of a patient, the messaging module 404 sends the text message to the cellular carrier (or cellular service provider) of the mobile device of the patient. The messaging module 404 may send the text message to the cellular carrier over a network, such as the Internet or a cellular network. Cellular carriers are illustrated by 416 in FIG. 4. The cellular carriers 416 transmit text messages from the messaging module 404 to their respective mobile device customers via a cellular network. The cellular carriers 416 also receive text messages from their respective mobile device customers and transmit the received text messages to the intended recipients (e.g., the TFNs of the pharmacy) directly or indirectly. Example mobile devices (e.g., cellular phones) are illustrated by 420 in FIG. 4.

Each patient served by the high volume pharmacy has a patient profile. A plurality of patient profiles 424 are shown in FIG. 4. The patient profiles 424 are stored in memory, such as in the storage devices 110. One example patient profile 504 is illustrated in FIG. 5.

The patient profiles 424 each include various fields, such as a name of the patient (Patient), a name of a prescription drug prescribed to the patient (Drug), a prescribed therapy for administering the prescription drug to the patient (Therapy), and a number of authorized refills remaining for the prescription. Each time that the pharmacy ships a refill to the patient, the order processing device 114 decrements the number of authorized refills remaining by one. In various implementations, multiple names of multiple prescription drugs and associated prescribed therapies may be stored in the patient profile 424.

The patient profiles 424 also include a number of refills already performed with the therapy remaining unchanged (Length of Unchanged Therapy), an opt into text messaging flag (Opt Into Text Messaging), an RBT flag, a toll free number (TFN) used for text messaging with the patient, an email address of the patient (Email), a mailing address of the patient (Mailing Address), billing information of the patient (Billing information), and a mobile phone number of the patient (Mobile Number). The patient profiles 424 may also include one or more other fields for other types of data.

The opt into text messaging flag may be set by the order processing device 114 to false by default and may be set to true, for example, in response to the patient authorizing the pharmacy to send text messages to the mobile phone number of the patient. The patient may authorize the pharmacy to send text messages electronically (e.g., in response to a text message or email) or verbally (e.g., during a voice call with a representative of the pharmacy).

The number of refills already performed with the therapy remaining unchanged count indicates how many consecutive times the patient has refilled or provided a new prescription for the therapy of the prescription drug without the therapy or the prescription drug changing. Each time that the pharmacy ships a refill or a new prescription to the patient without the therapy or the prescription drug changing, the order processing device 114 increments the number of refills already performed with the therapy remaining unchanged by one. When the therapy or the prescription drug changes, the order processing device 114 resets the number of refills already performed with the therapy remaining unchanged count to zero.

The toll free number (TFN) is the toll free number used by the pharmacy to send text messages to the patient at the mobile number and to receive text messages from the patient at the mobile number. When a text message is received by a toll free number of the pharmacy from a mobile number, the order processing device 114 identifies the associated patient profile based on the TFN that received the text message and the mobile number of the sender of the text message (that the TFN received the text message from).

The mailing address of the patient may include a street name and number, unit or suite number, city, state, and zip code where the pharmacy is to ship prescriptions and refills of the prescription drug to the patient. The billing information of the patient includes payment information (e.g., credit or debit card of the patient or bank account number and routing number of the patient's bank) and billing address information of the patient. The billing address may include a street name and number, unit or suite number, city, state, and zip code of the patient.

The RBT flag indicates whether the patient is enrolled in the RBT program or not. Alternatively, the RBT flag may indicate whether the patient is enrolled in another active text messaging program with the pharmacy or not. The RBT flag may be set to false (or no) by default. The order processing device 114 may set the RBT flag to true under some circumstances, as discussed further below. When the RBT flag is set to true (or yes), the order processing device 114, when a refill of the prescription drug is authorized by the benefits manager, sends a text message to the patient's mobile phone number asking the patient whether they'd like the pharmacy to refill the prescription drug and ship the refill to the patient. If the patient responds from the patient's mobile phone number with a text message having a predetermined affirmative response, the order processing device 114 triggers filling of the refill and shipping of the refill to the patient at the patient's mailing address.

Figure 6:
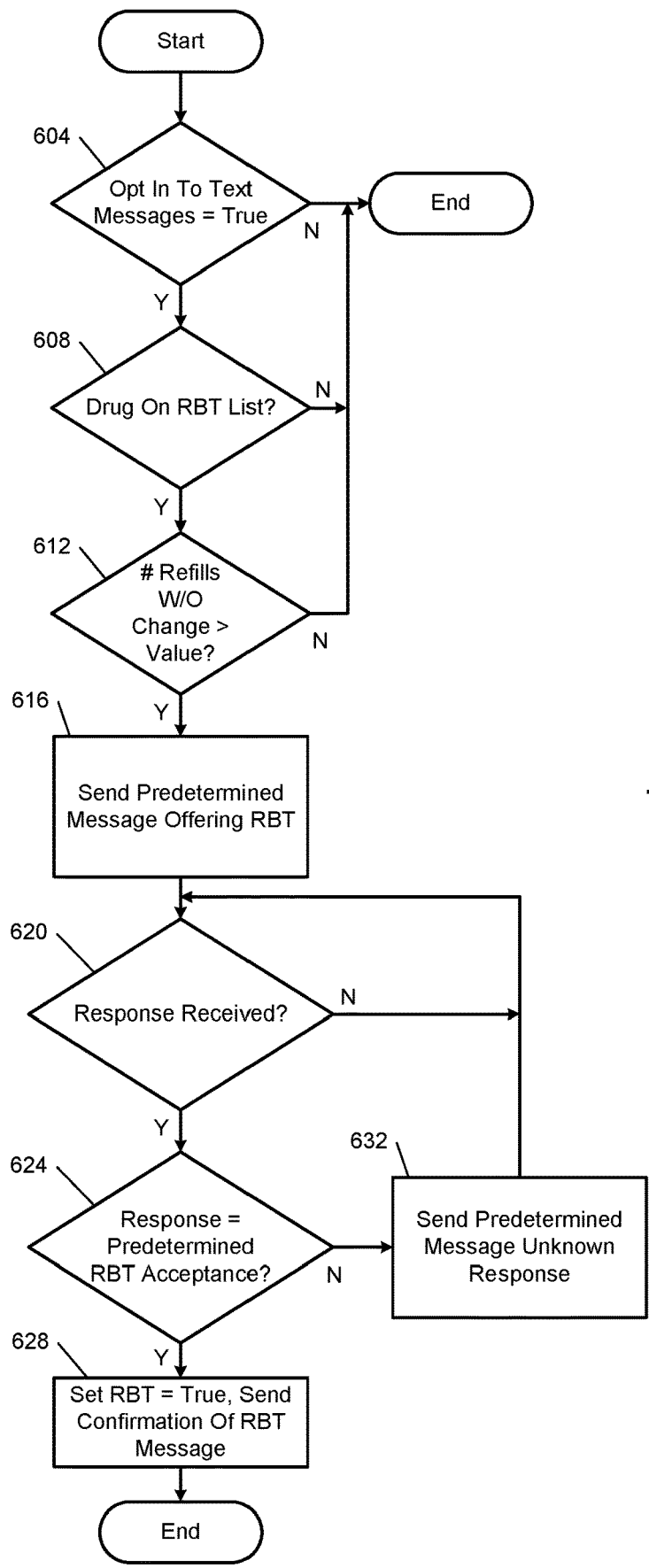
FIG. 6 is a flowchart depicting an example method of controlling whether a patient is enrolled in a RBT program.

FIG. 6 is a flowchart depicting an example method of controlling whether a patient is enrolled in the RBT program. As stated above, the RBT flag of the patient's patient profile may be set to false (or no) by default. The RBT flag may therefore be set to false where control begins at 604.

At 604, the RBT module 408 determines whether the opt into text messaging flag of the patient profile of the patient is set to true (or yes). If 604 is true, control continues with 608. If 604 is false the RBT module 408 sets (or maintains) the RBT flag of the patient profile of the patient to false, and control may end. The RBT module 408 may also set (or maintain) the opt into text messaging flag of the patient profile to false.

The RBT module 408 determines the drug prescribed to the patient from the patient profile and determines whether that drug is included in a RBT drug list 428 (FIG. 4) at 608. The RBT drug list 428 includes a list of prescription drugs that the pharmacy has approved for offering refills via text messaging. Prescription drugs not on the RBT drug list 428 cannot be refilled via only text messages. Prescription drugs that are not on the RBT drug list 428, however, can be refilled in other ways, such as via phone call with a representative of the pharmacy. If 608 is true, control continues with 612. If 608 is false, the RBT module 408 sets (or maintains) the RBT flag of the patient profile of the patient to false, and control may end. When the RBT flag is false, the patient cannot complete authorized refills of their prescription drug by only text messaging with the pharmacy.

At 612, the RBT module 408 determines whether the number of refills already performed with the therapy remaining unchanged (value) is greater than a predetermined value. The predetermined value is an integer greater than zero. The predetermined value may be, for example, 1, 2, or 3. The predetermined value being set to 2 or 3 may provide increased confidence that the therapy is properly prescribed to the patient. If 612 is true, control continues with 616. If 612 is false, the RBT module 408 sets (or maintains) the RBT flag of the patient profile of the patient to false, and control may end. Alternatively, the RBT module 408 may prompt the messaging module 404 to send a text message to the mobile number of the patient including a predetermined message requesting a response regarding whether to contact the patient's prescriber to obtain a renewal. In response to receipt of an affirmative response from the mobile number of the patient, the RBT module 408 may send a message to the prescriber electronically in an attempt to obtain authorization for a renewal of the prescription. Alternatively, the RBT module 408 may prompt a call center to initiate a call with the prescriber of the prescription to obtain authorization for a renewal of the prescription.

In various implementations, the RBT module 408 may determine whether the number of prescription drugs and therapies of the patient profile is less than or equal to a predetermined value. The RBT module 404 may not set the RBT flag of the patient profile to True if the number is greater than the predetermined number. In various implementations, the predetermined number may be 1, 2, or 3.

At 616, the RBT module 408 prompts the messaging module 404 to send a text message to the mobile number of the patient including a predetermined message offering the RBT program to the patient. The messaging module 404 obtains the mobile number of the patient from the patient profile of the patient. The messaging module 404 sends the text message to the patient from the TFN of the patient profile. The predetermined message offering the RBT program may state, for example, "Reply YES to start text refills for med starting with <X>. HELP for help. Not a condition of purchase. Auto Msg Freq varies. Msg & data rates apply." The messaging module 404 inserts the first letter of the name of the drug of the patient profile into the above text in place of <X>. The inclusion of only the first letter of the name of the drug may increase privacy.

At 620, the RBT module 408 determines whether the TFN from which the text message including the predetermined message offering the RBT program to the patient has received a text message response from the mobile number of the patient. If 620 is true, control continues with 624. If 620 is false, control may remain at 620. In various implementations, control may end if a response is not received within a predetermined period.

At 624, the RBT module 408 determines whether the text message response received from the mobile number at the TFN includes text indicative of an acceptance by the patient. For example, the RBT module 408 may determine whether the text included in the response text message is in an acceptance list 432 (FIG. 4). The acceptance list 432 includes a list of text responses that will be accepted to transition the RBT flag of the patient profile to true and to offer the filling of authorized refills to the patient via only text messages. The acceptance list 432 includes the requested reply included in the predetermined message offering the RBT program (YES) and may include one or more other options, such as ya, yup, yes please, yes thank you, etc. Capitalization may be ignored. Punctuation may also be ignored. Text in addition to an option that is in the acceptance list 432 may be ignored. If the text message response received from the mobile number at the TFN includes text indicative of a request for help, the messaging module 404 may send a text message to the mobile number of the patient including help information. The help information may state, for example, "These are texts about your medication. Call 1-877-YYY-YYYY to place orders, check status, or update info. Reply STOP to cancel." The messaging module 404 includes a phone number of the pharmacy in place of YYY-YYY-YYYY.

If 624 is true, the RBT module 408 sets the RBT flag of the patient profile to True at 628. The messaging module 404 also sends a text message to the mobile number of the patient from the TFN including a predetermined message indicative of a confirmation of the addition of the patient to the RBT program. The predetermined message indicative of a confirmation of the addition of the patient to the RBT program may state, for example, "OK, we'll start sending you texts to refill your medication starting with <X>. Reply STOP to Cancel, or Reply HELP for help." The messaging module 404 inserts the first letter of the name of the drug of the patient profile into the above text in place of <X>. If 624 is false, control may transfer to 632. The inclusion of only the first letter of the name of the drug may increase privacy. Alternatively, the RBT module 408 may set the RBT flag of the patient profile to True when the opt into text messaging flag of the patient profile is set to True.

At 632, the messaging module 404 may send a text message to the mobile number of the patient from the TFN including a predetermined message indicative of lack of understanding of the patient's response. The predetermined message indicative of a lack of understanding of the patient's response may state, for example, "Sorry, we didn't understand that response. Please reply YES to refill, HELP for help, or STOP to cancel the text reminders." Control may return to 620. While control is shown as ending, control may return to 604.

Figure 7:
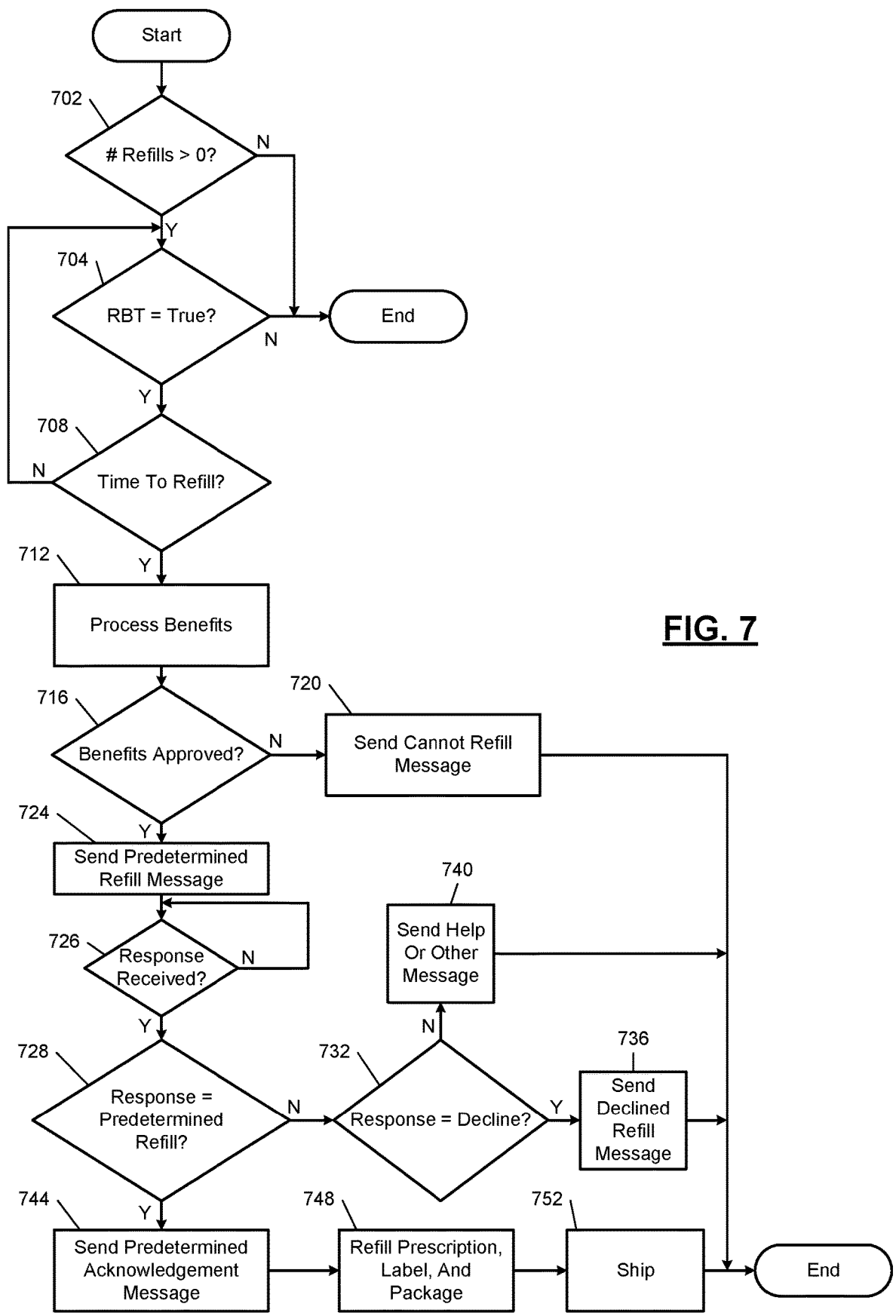
FIG. 7 is a flowchart depicting an example method of refilling a patient's prescription when the patient is enrolled in the RBT program.

FIG. 7 is a flowchart depicting an example method of refilling a patient's prescription when the patient is enrolled in the RBT program. Control begins with 702 where the RBT module 408 determines whether the number of authorized refills remaining for the patient of a patient profile is greater than zero. If 702 is false and the number of authorized refills remaining for the patient is zero, the messaging module 404 may transmit a text message to the mobile number of the patient from the TFN indicating that no authorized refills are remaining and that the patient should submit a new prescription order and control may end. If 702 is true, control continues with 704.

At 704, the RBT module 408 determines whether the RBT flag of the patient profile of the patient is set to true (or yes). If 704 is true, control continues with 708. If 704 is false, control may end. At 708, the RBT module 408 triggers the benefit manager device 102 to determine whether the patient is presently eligible to have an authorized refill of the prescription completed. The benefit manager device 102 determines whether the patient is presently eligible to have an authorized refill of the prescription completed in response to the triggering. For example only, the benefit manager device 102 may determine whether the number of days since the prescription (refill or new order) was last filled is greater than a predetermined number of days. If 708 is true, the RBT module 408 triggers the benefit manager device 102 to process the patient's benefits at 712, and control continues with 716. The processing of the patient's benefits may include adjudication, as described above.

At 716, the RBT module 408 determines whether the benefit manager device 102 approved the patient's benefits for the refilling of the patient's prescription. If 716 is false, control transfers to 720. If 716 is true, control continues with 724. At 720, the messaging module 404 sends a text message to the mobile number of the patient from the TFN including a predetermined message indicating that the pharmacy cannot complete the refill via text messaging. The predetermined message indicating that the pharmacy cannot complete the refill via text messaging may state, for example, "We are unable to fill your order at this time, please call 1-YYY-YYY-YYYY to complete your order. Reply STOP to cancel the text reminders." The messaging module 404 includes a phone number of the pharmacy in place of YYY-YYY-YYYY.

At 724, the messaging module 404 sends a text message to the mobile number of the patient from the TFN including a predetermined message inviting the patient to respond to initiate fulfillment of the refill of the prescription drug. The predetermined message inviting the patient to respond to initiate fulfillment of the refill of the prescription drug may state, for example, "Reply YES to refill your med starting with <X> to be shipped to the address starting with <123>. Reply STOP to remove this service or HELP" The messaging module 404 inserts the first letter of the prescription drug in place of <X>. The messaging module 404 inserts the street address of the patient in place of <123>. The inclusion of only the first letter of the name of the drug may increase privacy. The inclusion of only the first 3 characters of the street address of the patient may also increase privacy.

At 726, the RBT module 408 determines whether the TFN from which the text message including the predetermined message inviting the patient to respond to initiate fulfillment of the refill of the prescription drug has received a text message response from the mobile number of the patient. If 726 is true, control continues with 728. If 726 is false, control may remain at 726. In various implementations, control may end if a response is not received within a predetermined period.

At 728, the RBT module 408 determines whether the text message response received from the mobile number at the TFN includes text indicative of an acceptance by the patient. For example, the RBT module 408 may determine whether the text included in the response text message is in the acceptance list 432.

If 728 is true, control continues with 744. If 728 is false, control transfers to 732. At 732, the RBT module 408 determines whether the text message response received from the mobile number at the TFN includes text indicative of decline by the patient. For example, the RBT module 408 may determine whether the text included in the response text message includes "no" or other text declining the invitation to refill the patient's prescription by text messaging. If 732 is false, at 736 the messaging module 404 sends a text message to the mobile number of the patient from the TFN including a predetermined message confirming the patient's denial of the opportunity to refill the patient's prescription by text message. The predetermined message confirming the patient's denial of the opportunity to refill the patient's prescription by text message may state, for example, "Ok, you have declined your order at this time, please call 1-YYY-YYY-YYYY when you are ready to refill your medication." The messaging module 404 includes a phone number of the pharmacy in place of YYY-YYY-YYYY. The RBT module 408 may also set the RBT flag of the patient profile to false at 736. If 732 is false, at 740 the messaging module 404 may send a text message to the mobile number of the patient from the TFN including the predetermined help information or the predetermined message indicative of lack of understanding of the patient's response, depending on the text of the response.

At 744, the messaging module sends a text message to the mobile number of the patient from the TFN including a predetermined message confirming the initiation of the refill. The predetermined message confirming the initiation of the refill may state, for example, "Great, you will be notified when your med starting with <X> ships. If you have any questions call us at 1-YYY-YYY-YYYY. Reply STOP to cancel." The messaging module 404 inserts the first letter of the name of the drug of the patient profile into the above text in place of <X>. The messaging module 404 includes a phone number of the pharmacy in place of YYY-YYY-YYYY. The inclusion of only the first letter of the name of the drug may increase privacy.

At 748, the RBT module 408 prompts the pharmacy fulfillment devices 112 to refill the patient's prescription (e.g., fill a bottle), generate and apply appropriate labeling, and package the prescription and accompanying text for shipping. At 752, the pharmacy ships the refilled prescription to the patient by depositing the packaged and labeled prescription to a shipping service (e.g., USPS, FedEx, UPS, DHL) or a delivery service. The messaging module 404 may also send a text message to the patient including a predetermined message at 752. The predetermined message may indicate that the refill has shipped and also include a tracking number for the package. While control is shown as ending, control may return to 704, for example, for a next patient.

Figure 8:
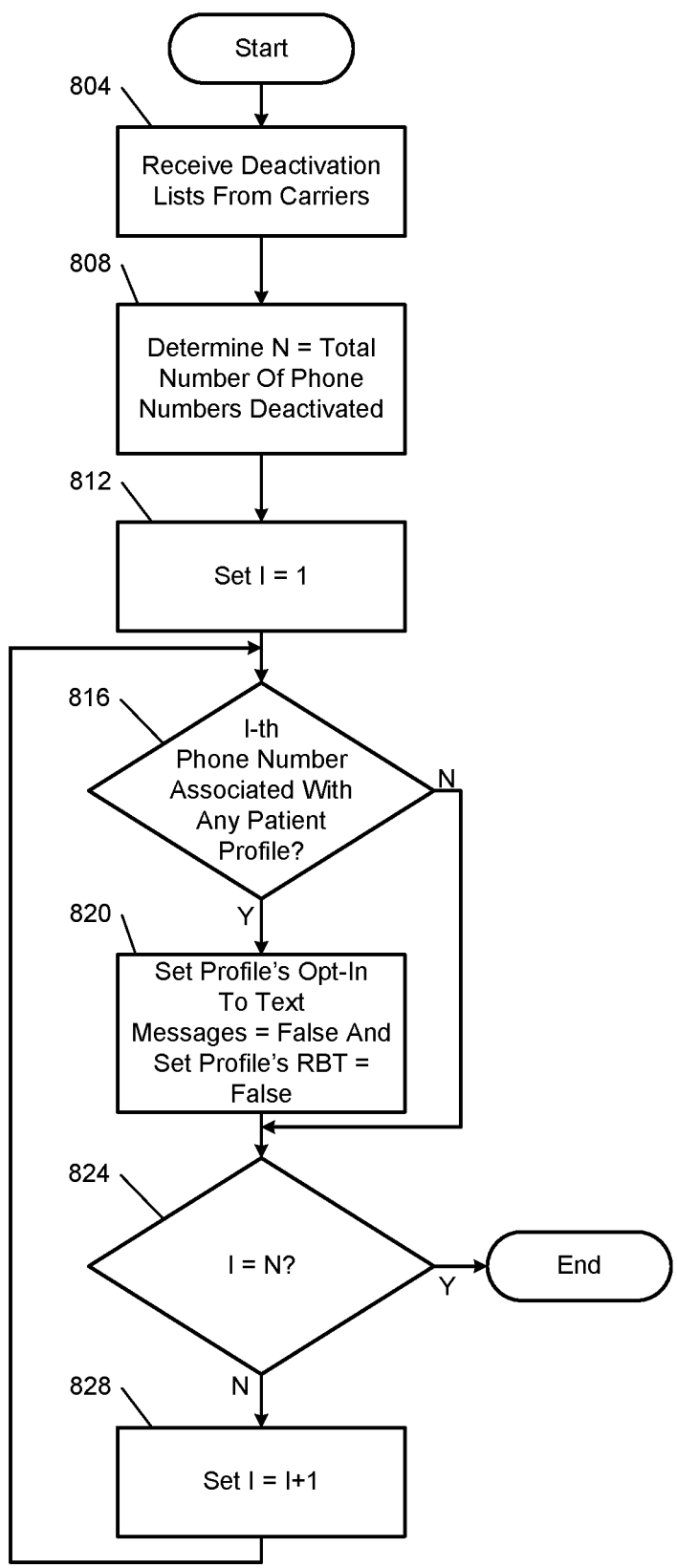
FIG. 8 is a flowchart depicting an example method of removing patients from the RBT program when mobile numbers associated with the patients, respectively, are deactivated by cellular service providers.

FIG. 8 is a flowchart depicting an example method of removing patient profiles from the RBT program when mobile numbers associated with the patient profiles, respectively, are deactivated by the cellular carriers 416.

Each of the cellular carriers 416 periodically (e.g., daily, weekly, etc.) generates and outputs its own a deactivated mobile numbers list 436 (FIG. 4). The deactivated mobile numbers list 436 of a carrier includes the mobile numbers of that carrier that were deactivated since the last time that carrier generated and output its deactivated mobile numbers list. In other words, the deactivated mobile numbers list 436 of a carrier includes the mobile numbers that are no longer provided cellular (or mobile) telephone service by the carrier. Due to the deactivation, the carrier will not deliver text messages to mobile numbers on the deactivated mobile numbers list 436 of the carrier. Each of the cellular carriers 416 may output its deactivated mobile numbers list to predetermined recipients (e.g., the pharmacy), upload its deactivated mobile numbers list to a predetermined location (e.g., a predetermined webpage), or make its deactivated mobile numbers list generally available. At 804, the messaging module 404 obtains or receives the deactivated mobile numbers lists 436 from the cellular carriers 416.

At 808, the messaging module 404 determines N, which is the total number of mobile numbers on all of the deactivated mobile numbers lists 436. For example, the messaging module 404 may count (sum) the number of mobile numbers on the deactivated mobile numbers lists 436. At 812, the messaging module 404 sets 1=1.

At 816, the messaging module 404 selects the I-th one of the deactivated mobile numbers on the deactivated mobile numbers lists 436 and determines whether the I-th one of the deactivated mobile numbers is in any one of the patient profiles 424. If 816 is true, control continues with 820. If 816 is false, control continues with 824. At 820, the messaging module 404 sets the RBT flag and the opt into text messages flag of the one of the patient profiles with the I-th one of the deactivated mobile numbers to false, and control continues with 824. Based on the opt into text messages flag being set to false, the messaging module 404 will not send text messages to the mobile number of that one of the patient profiles. Based on the RBT flag being set to false, the messaging module 404 will not send text messages regarding the RBT program to the mobile number of that one of the patient profiles.

At 824, the messaging module 404 determines whether I is equal to N (the total number of deactivated mobile numbers). If 824 is true, control may end until the next time that one or more of the deactivated mobile numbers lists 436 is generated and output. If 824 is false, the messaging module 404 increments I (e.g., sets I=I+1) at 828, and control returns to 816. In this way, each of the mobile numbers on the deactivated numbers lists 436 is checked for inclusion in the patient profiles 424.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system for refilling prescription drugs by text messaging, the system comprising:
   a non-transitory computer-readable medium storing patient profiles for patients, respectively, each of the patient profiles including at least:

a name of a patient;
   a name of a prescription drug prescribed to the patient;
   a number of authorized refills of the prescription drug presently available to the patient;
   a number of refills of the prescription drug already provided to the patient without a change in a therapy of the prescription drug;
   a mobile phone number of the patient;
   a first indicator indicative of whether the patient has opted into receiving text messages; and
   a second indicator indicative of whether the patient is included in a refill by text program;
a messaging module configured to, in response to the first indicator indicating that the patient has opted into receiving text messages, selectively send text messages to the mobile phone number of the patient and to receive text messages from the mobile phone number of the patient; and
a refill by text module configured to, when the second indicator indicates that the patient is not included in the refill by text program, trigger the messaging module to send a first predetermined text message to the mobile phone number of the patient in response to a determination that:
   the name of the prescription drug prescribed to the patient is included in a stored list of prescription drugs associated with the refill by text program;
   the first indicator indicates that the patient has opted into receiving text messages; and
   the number of refills of the prescription drug already provided to the patient without a change in the therapy of the prescription drug is greater than a predetermined number,
wherein the first predetermined text message offers entry into the refill by text program to the patient,
wherein the messaging module is configured to send the first predetermined text message to the mobile phone number of the patient in response to the triggering by the refill by text module,
wherein the refill by text module is further configured to:
   change the second indicator to indicate that the patient is included in the refill by text program in response to receiving a text message from the mobile phone number of the patient including an affirmative response to the first predetermined text message; and
   when the second indicator indicates that the patient is included in the refill by text program and the number of authorized refills of the prescription drug presently available to the patient is greater than zero, trigger the messaging module to send a second predetermined text message to the mobile phone number of the patient,
   wherein the second predetermined text message requests a response indicative of whether the patient would like to initiate a refill of the prescription drug,
wherein the messaging module is configured to send the second predetermined text message to the mobile phone number of the patient in response to the triggering by the refill by text module.

2. The system of claim 1 wherein the refill by text module is configured to trigger the messaging module to send the second predetermined text message to the mobile phone number of the patient in response to a determination that:
   the second indicator indicates that the patient is included in the refill by text program;
   the number of authorized refills of the prescription drug presently available to the patient is greater than zero; and
   a period since a last refill of the prescription drug by the patient is greater than a predetermined period.

3. The system of claim 1 wherein the messaging module sends text messages to the mobile phone number of the patient from a toll free number (TFN) and receives text messages from the mobile phone number of the patient at the TFN.

4. The system of claim 1 wherein the first predetermined text message includes the text:
   Reply YES to start text refills for med starting with <X>,
   wherein the messaging module inserts a first letter of the name of the prescription drug in place of <X>.

5. The system of claim 1 wherein the refill by text module is configured to trigger the messaging module to send a third predetermined text message to the mobile phone number of the patient in response to receiving a text message including an unknown response to the first predetermined text message.

6. The system of claim 1 wherein the refill by text module is configured to change the second indicator to indicate that the patient is included in the refill by text program in response to receiving a text message including an affirmative response to the first predetermined text message and verifying that the affirmative response is included in a stored list of affirmative responses.

7. The system of claim 1 wherein the second predetermined text message includes the text:
   Reply YES to refill your med starting with <X> wherein the messaging module inserts a first letter of the name of the prescription drug in place of <X>.

8. The system of claim 1 wherein the second predetermined text message includes the text:
   Reply YES to refill your med starting with <X> to be shipped to the address starting with <123>,
   wherein the messaging module inserts a first letter of the name of the prescription drug in place of <X> and inserts a street address of the patient in place of <123>.

9. The system of claim 1 further comprising at least one pharmacy fulfillment device configured to package the prescription drug for shipment to the patient in response to being triggered by the refill by text module,
   wherein the refill by text module is configured to trigger the at least one pharmacy fulfillment device in response to receiving a text message from the mobile phone number of the patient including an affirmative response to the second predetermined text message.

10. The system of claim 9 wherein the refill by text module is configured to trigger the at least one pharmacy fulfillment device in response to receiving a text message from the mobile phone number of the patient including an affirmative response to the second predetermined text message and verifying that the affirmative response is included in a stored list of affirmative responses.

11. The system of claim 10 wherein the at least one pharmacy fulfillment device is configured to dispense the prescription drug into a bottle in response to being triggered by the refill by text module.

12. The system of claim 10 wherein the at least one pharmacy fulfillment device is configured to apply a shipping label to the package in response to being triggered by the refill by text module.

13. The system of claim 1 wherein the messaging module is further configured to:

receive a deactivated mobile numbers list from a cellular service provider; and in response to a determination that the mobile phone number of the patient is included in the deactivated mobile numbers list:

set the first indicator to indicate that the patient has not opted into receiving text messages; and set the second indicator to indicate that the patient is not included in the refill by text program.

14. A method, comprising:

Selectively accessing a non-transitory computer-readable medium storing patient profiles for patients, respectively, each of the patient profiles including at least:

a name of a patient;

a name of a prescription drug prescribed to the patient;

a number of authorized refills of the prescription drug presently available to the patient;

a number of refills of the prescription drug already provided to the patient without a change in a therapy of the prescription drug;

a mobile phone number of the patient;

a first indicator indicative of whether the patient has opted into receiving text messages; and a second indicator indicative of whether the patient is included in a refill by text program;

in response to the first indicator indicating that the patient has opted into receiving text messages, selectively sending text messages to the mobile phone number of the patient and receiving text messages from the mobile phone number of the patient;

when the second indicator indicates that the patient is not included in the refill by text program, sending a first predetermined text message to the mobile phone number of the patient in response to a determination that:

the name of the prescription drug prescribed to the patient is included in a stored list of prescription drugs associated with the refill by text program;

the first indicator indicates that the patient has opted into receiving text messages; and the number of refills of the prescription drug already provided to the patient without a change in the therapy of the prescription drug is greater than a predetermined number, wherein the first predetermined text message offers entry into the refill by text program to the patient;

changing the second indicator to indicate that the patient is included in the refill by text program in response to receiving a text message from the mobile phone number of the patient including an affirmative response to the first predetermined text message; and when the second indicator indicates that the patient is included in the refill by text program and the number of authorized refills of the prescription drug presently available to the patient is greater than zero, sending a second predetermined text message to the mobile phone number of the patient, wherein the second predetermined text message requests a response indicative of whether the patient would like to initiate a refill of the prescription drug.

15. The method of claim 14 wherein sending the second predetermined text message includes sending the second predetermined text message to the mobile phone number of the patient in response to a determination that:

the second indicator indicates that the patient is included in the refill by text program;

the number of authorized refills of the prescription drug presently available to the patient is greater than zero; and a period since a last refill of the prescription drug by the patient is greater than a predetermined period.

16. The method of claim 14 further comprising sending text messages to the mobile phone number of the patient from a toll free number (TFN) and receiving text messages from the mobile phone number of the patient at the TFN.

17. The method of claim 14 wherein the first predetermined text message includes the text:

Reply YES to start text refills for med starting with <X>, wherein the method further includes inserting a first letter of the name of the prescription drug in place of <X>.

18. The method of claim 14 further comprising sending a third predetermined text message to the mobile phone number of the patient in response to receiving a text message including an unknown response to the first predetermined text message.

19. The method of claim 14 further comprising changing the second indicator to indicate that the patient is included in the refill by text program in response to receiving a text message including an affirmative response to the first predetermined text message and verifying that the affirmative response is included in a stored list of affirmative responses.

20. The method of claim 14 wherein the second predetermined text message includes the text:

Reply YES to refill your med starting with <X> wherein the method further includes inserting a first letter of the name of the prescription drug in place of <X>.

21. The method of claim 14 wherein the second predetermined text message includes the text:

Reply YES to refill your med starting with <X> to be shipped to the address starting with <123>, wherein the method further includes inserting a first letter of the name of the prescription drug in place of <X> and inserts a street address of the patient in place of <123>.

22. The method of claim 14 wherein further comprising, by at least one pharmacy fulfillment device, packaging the prescription drug for shipment to the patient in response to receiving a text message from the mobile phone number of the patient including an affirmative response to the second predetermined text message.

23. The method of claim 14 further comprising, by at least one pharmacy fulfillment device, packaging the prescription drug for shipment to the patient in response to receiving a text message from the mobile phone number of the patient including an affirmative response to the second predetermined text message and verifying that the affirmative response is included in a stored list of affirmative responses.

24. The method of claim 23 further comprising, by the at least one pharmacy fulfillment device, dispensing the prescription drug into a bottle in response to receiving the text message from the mobile phone number of the patient including the affirmative response to the second predetermined text message and verifying that the affirmative response is included in the stored list of affirmative responses.

25. The method of claim 23 further comprising, by the at least one pharmacy fulfillment device, applying a shipping label to the package in response to receiving the text message from the mobile phone number of the patient including an affirmative response to the second predetermined text message and verifying that the affirmative response is included in the stored list of affirmative responses.

26. The method of claim 14 further comprising:
receiving a deactivated mobile numbers list from a cellular service provider; and
in response to a determination that the mobile phone number of the patient is included in the deactivated mobile numbers list:
  setting the first indicator to indicate that the patient has not opted into receiving text messages; and
  setting the second indicator to indicate that the patient is not included in the refill by text program.

* * * * *